United States Patent [19]

Ritch et al.

[11] Patent Number: 4,968,296
[45] Date of Patent: Nov. 6, 1990

[54] TRANSSCLERAL DRAINAGE IMPLANT DEVICE FOR THE TREATMENT OF GLAUCOMA

[76] Inventors: Robert Ritch, 455 E. 57th St., New York, N.Y. 10022; Edward E. Klein, 12 Haights Cross Rd., Chappaqua, N.Y. 10514

[21] Appl. No.: 454,013
[22] Filed: Dec. 20, 1989
[51] Int. Cl.⁵ .............................................. A61M 5/00
[52] U.S. Cl. ........................................ 604/8; 604/164; 604/264; 604/294; 606/108
[58] Field of Search ........................... 604/8–11, 604/15–18, 49, 104, 164, 175, 264, 272, 274, 280, 294; 623/4; 606/108, 109

[56] References Cited

U.S. PATENT DOCUMENTS

| | | | |
|---|---|---|---|
| 3,530,860 | 9/1970 | Majoros | 606/109 |
| 3,788,327 | 1/1974 | Donowitz et al. | 604/9 X |
| 3,884,238 | 5/1975 | O'Malley | 128/305 |
| 3,913,584 | 10/1975 | Walchle et al. | 604/164 X |
| 3,948,271 | 4/1976 | Akiyama | 604/264 X |
| 4,037,604 | 7/1977 | Newkirk | 604/9 |
| 4,168,697 | 9/1979 | Cantekin | 604/264 X |
| 4,530,356 | 7/1985 | Helfgott et al. | 128/305 |
| 4,530,359 | 7/1985 | Helfgott et al. | 128/329 R |
| 4,590,935 | 5/1986 | Ranalli | 128/305 |
| 4,674,502 | 6/1987 | Imonti | 128/305 |
| 4,744,364 | 5/1988 | Kensey | 604/15 X |
| 4,750,901 | 6/1988 | Molteno | 604/8 |
| 4,753,234 | 6/1988 | Martinez | 128/305 |
| 4,787,885 | 11/1988 | Binder | 604/8 |
| 4,842,585 | 6/1989 | Witt | 604/158 |
| 4,900,303 | 2/1990 | Lemelson | 604/54 |
| 4,936,825 | 6/1990 | Ungerleider | 604/8 |

OTHER PUBLICATIONS

Ellis, Richard A., "Reduction of Intraocular Pressure Using Plastics in Surgery", *American Journal of Opthamology*, vol. 50, 1960, pp. 733–742.

Primary Examiner—John D. Yasko
Assistant Examiner—Adam J. Cermak
Attorney, Agent, or Firm—Mark T. Basseches; Paula T. Basseches

[57] ABSTRACT

A method of permanently surgically treating glaucoma is disclosed together with an apparatus for effecting such treatment. In accordance with the method, an implant is disposed at a filtration site through the sclera the implant including a through going aperture leading from the anterior chamber to a bleb formed in the conjunctiva. The implant is retained in the sclera by radially compressing the same during the insertion procedure and thereafter releasing the radial compressive forces whereby the implant expands and is prevented from dislocation. An apparatus for effecting the implant is likewise disclosed, the apparatus including a cannula having a bore constraining the insert, a plunger for shifting the insert through an angularly offset opening in the cannula and a retainer filament engaged in the passage in the insert for controlling the precise location of the insert during the implant and for releasing the insert from connection to the cannula when the precise position is achieved.

10 Claims, 3 Drawing Sheets

TRANSSCLERAL DRAINAGE IMPLANT DEVICE FOR THE TREATMENT OF GLAUCOMA

BACKGROUND OF THE INVENTION

The present invention is directed to a method and apparatus for the treatment of glaucoma and relates more particularly to a method of surgically treating glaucoma and to the apparatus for effecting such treatment.

PRIOR ART

Glaucoma is a leading cause of blindness. While the term "glaucoma" is applied to a large number of different disorders of the eye, common to all types of glaucoma is the phenomenon in which pressure within the eye elevates with resultant destruction of the optic nerve. In most forms of glaucoma the pressure elevation is not sensed by the individual, such as by pain or reduced visual acuity until significant loss of vision has occurred.

In the healthy eye, fluid (aqueous humor) passes from the anterior chamber through a filter-like mass of tissue (the trabecular meshwork) and thence to a connected series of veins in the sclera.

In the most commonly encountered form of glaucoma (open-angle glaucoma) the pressure elevation results from a blockage of the outflow pathway through the trabecular meshwork.

Methods of treating glaucoma have taken two general forms, namely medication and surgery. Each of the noted treatment methods and techniques as heretofore practiced are accompanied by significant drawbacks.

There are four categories of drugs currently in use for the control of glaucoma. Miotics (pilocarpine and carbachol) are administered as drops applied locally and function to tighten the muscle fibers of the trabecular meshwork to increase the rate at which the aqueous humor leaves the eye. Despite limited side effects of miotics, younger patients frequently suffer induced myopia and fluctuating vision. These drugs must be taken four times a day and patients often have difficulty with compliance with the frequent self-administration of such drugs.

A second category of compounds (epinephrine) have been successful in reducing intraocular pressure. However, many patients experience headaches, pain, and ocular irritation, hypertension, palpitations, and sweating.

A further category of drugs known as beta-adrenergic blocking agents function in a somewhat different manner. These drugs, employed as drops, decrease the production of aqueous humor and thus reduce pressure by decreasing the rate of flow of fluid into the eye and subsequently through the meshwork. Drugs of this category may exacerbate asthma and other pulmonary conditions, induce congestive heart failure, depression, insomnia, fatigue, and loss of memory.

The last major category of drug therapy or glaucoma employs carbonic anhydrase inhibitors as pills. These drugs function to decrease aqueous secretion but have extensive side effects including weight loss, gastrointestinal upset, depression, impotence and predisposition to renal stones.

Because tolerance may develop to medications continuous monitoring and frequent changing of dosages is often required. Very often drugs alone are insufficient to control glaucoma.

Accepted surgical treatments of glaucoma include laser treatment of the trabecular meshwork (trabeculoplasty). In this procedure, a laser treatment is applied to the internal portion of the trabecular tissues, increasing the rate of aqueous outflow through the trabecular network. This laser procedure is generally used when the patient is unable to tolerate medication or if medication is insufficient to control the glaucoma. Initial success rates of 80 to 90 percent are observed using the laser procedure. However, laser treatment is generally regarded as a temporary cure and generally wears off at the rate of about 7% per year due to healing. Repeating the procedure may lead to worsening of the disease.

If the glaucoma cannot be controlled by either medication or laser treatment, surgical intervention is indicated. The most common operation for glaucoma is trabeculectomy. This procedure involves forming an incision in the conjunctiva and underlying tenon's capsule to expose the sclera. After the sclera has been exposed a scleral flap is dissected beginning posteriorly and leading forward into the cornea. The flap is elevated and a rectangular ridge of trabecular meshwork approximately 3 mm long and 1 to 1.5 mm wide is excised. An iridectomy is performed in the peripheral iris to prevent blockage of the trabeculectomy opening and the scleral flap is sutured back in place. The incisions in the conjunctiva and tenon's capsule are thereafter closed. There is a high incidence of subsequent failure, such failures occurring at any time between a few weeks after the operation to years later. Failures most frequently result from scarring at the site of the incisions in the conjunctiva and the tenon's capsule.

In a surgical technique known as the Molteno implant, a leakage path is formed by inserting a tube through a flap in the sclera and conjunctiva, the tube extending into the anterior chamber. The tube is retained in position by sutures placed through the sclera and looped around the tube, the scleral flap being sutured back in place and the conjunctiva closed. In addition to such procedure being difficult to perform, the formation of incisions in the sclera and conjunctiva engender the difficulties noted above in respect of conventional trabeculectomy techniques.

A more comprehensive consideration of the various glaucoma surgery techniques may be derived from a leading text on the subject co-authored by a co-inventor hereof, namely "The Glaucomas" (R. Ritch, M. B. Shields, T. Krupin), C. V. Mosby co, St. Louis 1989.

It has been proposed, in accordance with certain experimental surgical techniques, to minimize surgical trauma to the overlying episcleral tissues and avoid the formation of a conjunctival incision by effecting an internal (ab-interno) filtration surgery procedure. Such a technique is described in volume 1 number 2 December 1988 page 199, issue "Opthalmology Clinics of North America" in an article by R. H. Brown and M. G. Lynch. The technique described in such reference involves performing a filtering operation from within the anterior chamber utilizing a trephine which is capable of simultaneous cutting and irrigation. The device is brought into the anterior chamber through a limbal incision 180 away from the planned sclerectomy site. The device is inserted through the incision across the anterior chamber above the iris and into a previously formed bleb raised in the conjunctiva in register with the intended filtration site. The device removes a core or plug of the sclera which after removal is discharged into the bleb.

The above described technique is said to minimize many of the drawbacks inherent in surgical procedures of the conventional type (performed from the exterior) described above. The noted experimental procedures however, have given rise to still other types of difficulties including particularly the tendency of the scleral fistula to progressively narrow over a period of time with resultant progressive loss of filtration effectiveness. Numerous variations of the surgical techniques generally described above have been attempted with mixed success. Heretofore, advantages of each of the techniques have been accompanied by concomitant adverse effects which have thus far limited the widespread acceptance of the procedures.

SUMMARY OF THE INVENTION

The present invention may be summarized as directed to a novel surgical method for the permanent treatment of glaucoma and to an apparatus for effecting such treatment. More specifically, the present invention is directed to a method of emplacing an implant having a through going passage at a filtration sight linking the anterior chamber of the eye with a subconjunctival bleb whereby aqueous humor from the anterior chamber may pass through the implant into the bleb formed in the conjunctiva from which the fluid filters into the body circulation.

In accordance with the method of the invention, there is provided an implant formed of relatively resilient polymeric material characterized in that the same includes a through going passage and has an exterior surface including a narrow neck portion and radially extending flanges adjacent the ends of the insert. The longitudinal extent of the neck portion is calculated to span the length of the fistula formed in the sclera. Implantation is effected, as will be more fully described hereinafter, by inserting a cannula containing the insert through clear cornea just anterior to the limbus to the desired filtration site in registry with a previously formed conjunctival bleb. The insert is contained in a cannula which retains the flanges of the insert in a radially inwardly deflected condition. With the neck of the insert in registry with the incision, the insert is ejected from the cannula, preferably in angular direction, whereupon the flanges are released to expand radially thereby to retain the insert at the filtration site.

The invention is further directed to a novel instrument for effecting the implant. The instrument is comprised of an elongate cannula having a discharge tip at one end. The tip includes a discharge opening which is preferably angularly oriented relative to the axis of the cannula. Preferably a deflector cam surface is disposed adjacent the discharge opening to insure a lateral as well as a forward deflection of the insert as the same is ejected. The insert is lodged within the bore of the cannula the flanges of the insert being retained in radially inwardly deflected position as a result of the relative sizing of the bore and flanges. A plunger is disposed within the cannula having a lead edge adjacent the innermost end of the insert. Within the plunger there is disposed an axially shiftable resilient filament the lead edge of which is preferably disposed within the passage of the insert.

The insert is emplaced by advancing the cannula such that the discharge opening spans the desired filtration site between the anterior chamber and bleb. When appropriately positioned the plunger and filament are shifted within the cannula in the direction of the discharge opening the insert thus being ejected, preferably angularly relative to the bore of the cannula. When the insert is free of the cannula bore, it is preferably frictionally retained on the filament. When the desired implantation site is accurately located, the filament is withdrawn from the insert and the cannula, plunger and filament bodily removed from the filtration site.

The insert is reliably retained at the filtration site and provides a permanent through going passage for relief of intraocular pressure.

Optionally, but preferably the lead edge of the cannula is sharpened to enable the formation of the fistula at the filtration site by manipulation of the cannula.

With the foregoing in mind, it is an object of the present invention to provide a method of and an apparatus for permanently treating glaucoma by providing a permanent passage through the sclera for the exit of aqueous humor.

DETAILED DESCRIPTION OF THE DRAWINGS

Figures 1, 2:
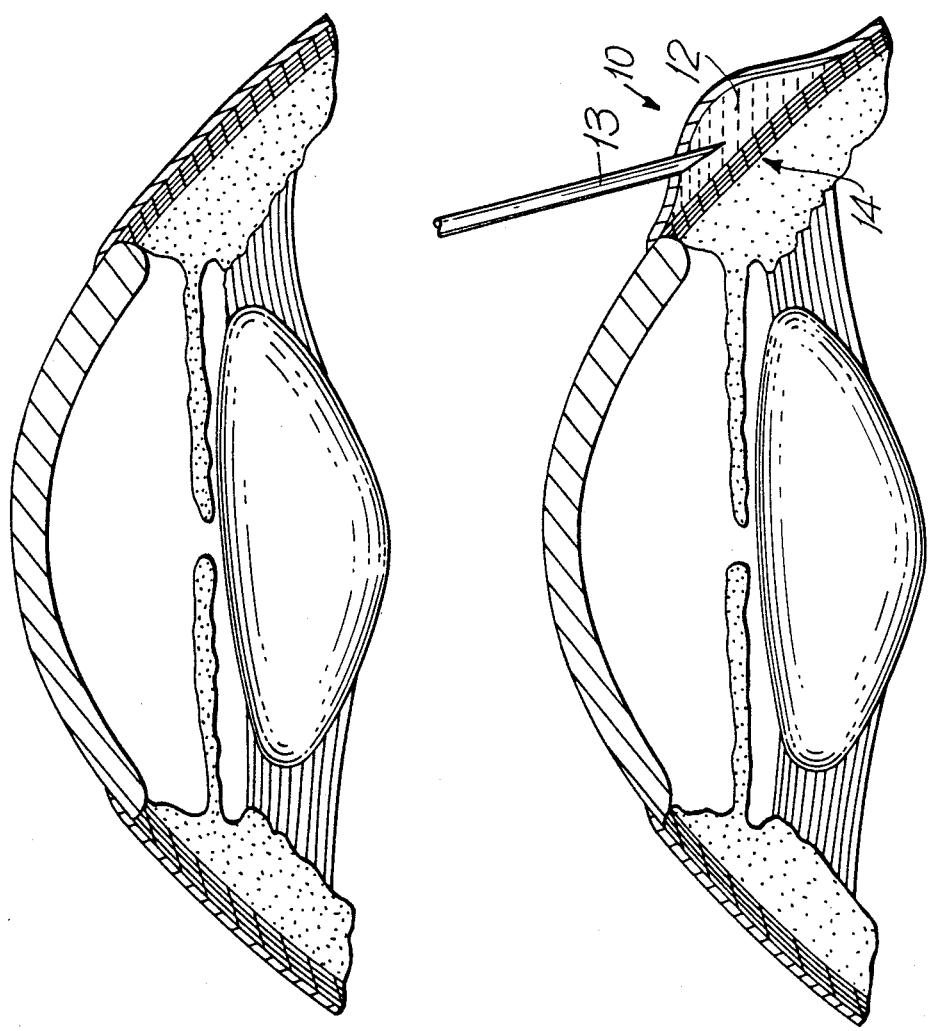
FIG. 1 is a schematic fragmentary sectional view or portion of the human eye.
FIG. 2 is a view similar to FIG. 1 illustrating the formation of a conjunctival bleb.
Figure 3:
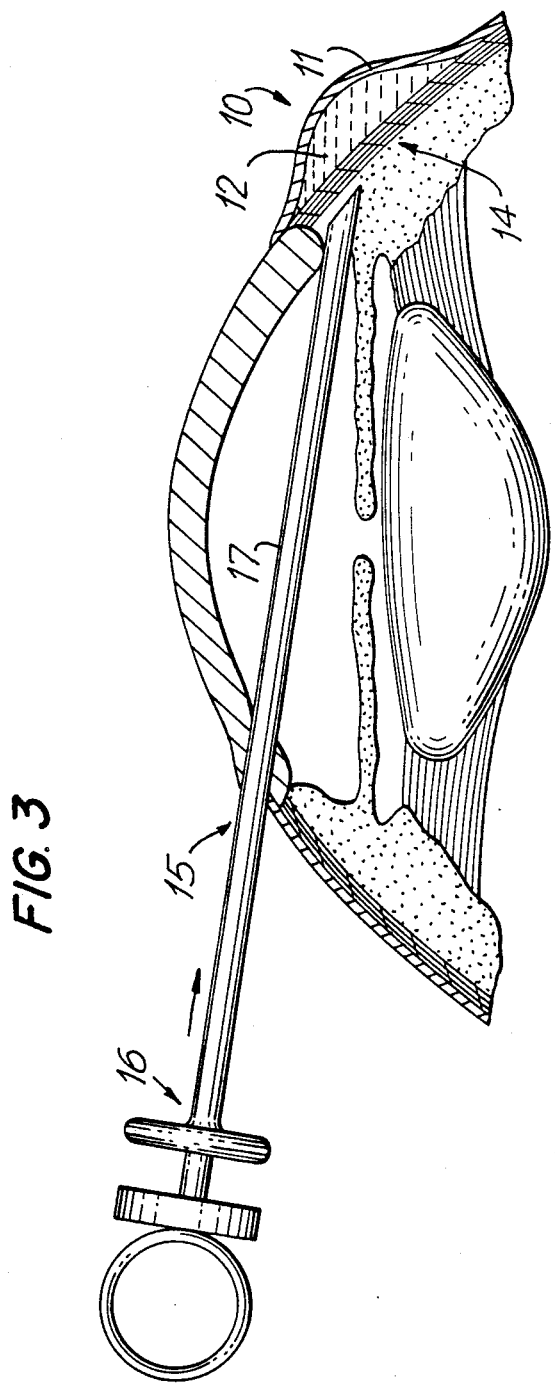
FIG. 3 is a view similar to FIG. 2 showing the implantation instrument inserted into the filtration site.

Referring now to the drawings there is shown in FIGS. 1 through 3 in schematic or diagrammatic fashion elements of the human eye in so far as germane to the instant procedure.

As shown in FIG. 2, as an initial step in the procedure a bleb 10 is formed in the conjunctiva 11 as by injecting saline 12 through a needle 13. The formation of a bleb is highly desirable in that by spacing the conjunctiva from the filtration site 14, inadvertent puncturing of the conjunctiva during implantation is avoided.

Following creation of the bleb, implantation is effected by initially forming a small (approximately 2 mm in length) incision 15 in the peripheral cornea inferiorly, approximately 1 mm from the limbus. The incision 15 is disposed opposite the filtration site 14 and is formed anterior of the limbus for the purpose of avoiding the necessity of making a conjunctival flap.

The implantation instrument 16 which will be described in detail hereinafter is advanced through the incision 15 to the filtration site 14. Preferably a viscoelastic substance such as HEALON is instilled in the anterior chamber to prevent collapse of the chamber during the procedure.

The cannula component 17 of the instrument 16 is advanced to the filtration site 14 and advanced through the sclera 18 to form a fistula 19 in registry with the bleb 10. Optionally, but preferably, the fistula 19 is formed by manipulating the sharpened lead edge 20 of the tip of the cannula against the sclera until a scleral puncture is achieved. The fistula may be formed as a separate procedure.

As will described in greater detail in connection with a description of the structure and function of the instrument 16, the insert member 21 is discharged from the cannula 17 when the discharge opening 22 formed in the tip of the instrument is in spanning relation of the sclera 18.

As will be more clearly apparent from an inspection of FIGS. 4A through 4D, the insert 21 which is comprised of a polymeric material, preferably Silastic, is generally in the shape of a dumbbell in longitudinal section including a central relatively narrow neck portion 23 and flanges 24,25 at the distal ends. The Silastic material, in the dimensions hereinafter set forth, provides a flaccid matrix having limited but significant memory characteristics. As will become clear from the ensuing detailed description of the insertion sequence, the insert 21, when subjected to radial compression, may be configured such that the flanges 24,25 may be aligned generally with the neck portion 23 but when freed from constraints will return to a condition in which the same stem radially outwardly beyond the neck portion. As will be appreciated particularly from an inspection of FIG. 4D, when the flanges 24,25 return to their radial outermost positions they will securely anchor the insert in the desired spanning position of the sclera.

Figure 4A:
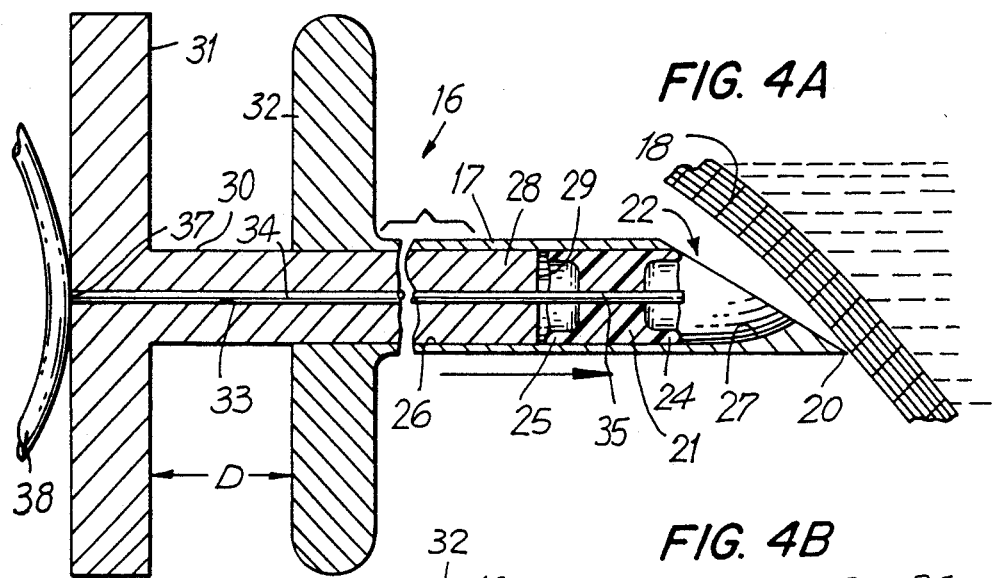
FIGS. 4A through 4D are schematic fragmentary sectorial views illustrating progressive stages of the implantation process.
Figure 4B:
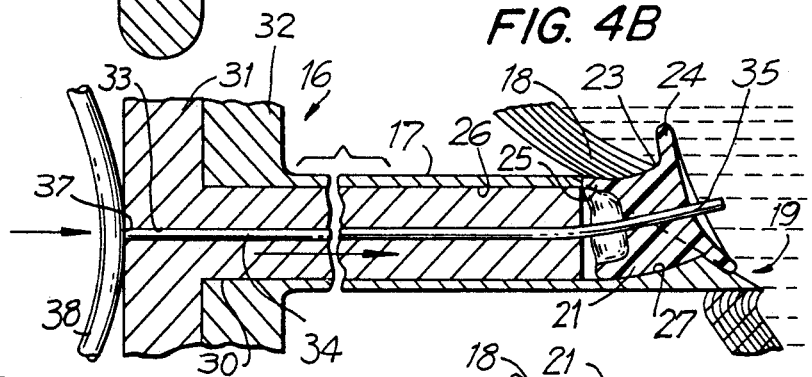
Figure 4C:
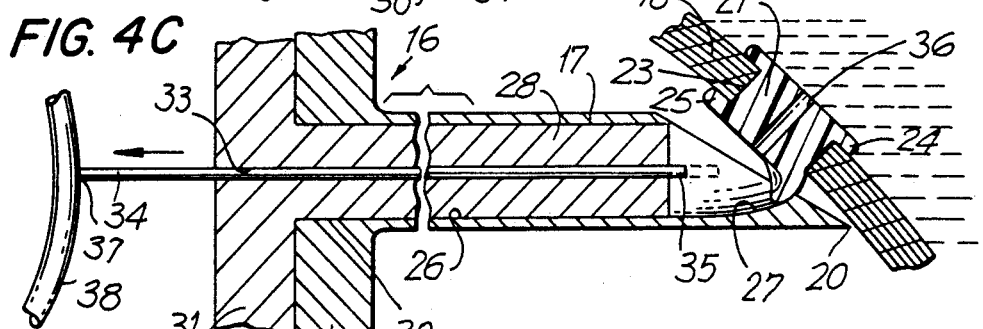

Turning next to FIGS. 4A through 4D, there is shown schematically sequential views of the various insertion steps, the views including in addition details of construction of the insertion device 16. More specifically, in FIG. 4A the components are illustrated as positioned to effect a puncture of the sclera 18. In FIG. 4B the insert 21 has been partially discharged from the instrument, contact between the instrument and insert being retained to permit precise location of the insert relative to the fistula 19 in the sclera. In FIG. 4C, the insert has been dislodged from the instrument whereas in FIG. 4D the insert is shown as in its final emplacement, the instrument having been partially withdrawn.

Referring now specifically to FIGS. 4A through 1D, the instrument 16 includes hollow cannula 17 having an internal bore 26. The cannula includes a sharpened tip 20 and a laterally angularly directed discharge opening 22. Preferably, a deflector cam surface 27 is disposed adjacent and directed toward the discharge opening 22.

Axially movably mounted within the cannula 17 is a discharge plunger 28 having a lead edge 29 disposed adjacent the trailing flange 25 of the insert member. The plunger includes at its outer end 30 a stop shoulder 31. Stop shoulder 31 is spaced a predetermined distance D (4A) from a complemental abutment 32 fixed to the cannula 17. The distance D is sufficient to assure ejection of the insert when the stop shoulder 31 is brought against the abutment 32. Preferably, the distance D is sufficiently small as to preclude advancing the insert entirely through the fistula 19.

The plunger 28 is hollow including an axially directed passage 33 within which is located an elongate resilient filament 34. The inner end 35 of the filament 34 is disposed within and preferably frictionally engages within the drainage passage 36 formed through the insert member 21. It will thus be observed that a degree of control of the position of the insert is achieved by virtue of the frictional connection between the filament 34 and insert 21.

The filament serves the additional function of assuring that the drainage aperture in the insert will not be clogged by tissue fragments during emplacement of the insert.

The outer end 37 of the filament 34 is connected to a release ring 38 whereby the filament may be shifted axially outwardly relative to the plunger 28.

Referring again to the sequential views FIGS. 4A through 4D with the parts positioned as in FIGS. 4A through 4D cannula tip 20 is passed through the sclera 18 preferably as a result of an incision effected utilizing the sharpened tip 20 as a cutting instrument. By appropriate manipulation of the cannula the tip 20 may function to form a flap of the material of the sclera or, when used in a less preferred manner, to excise a core component from the sclera. Optionally, in a non-preferred method, the aperture in the sclera may be formed as a prior step, i.e. by a trephine.

Following formation of the fistula, the cannula is adjusted such that the discharge opening 22 is aligned with the wall of the sclera (FIG. 4B). When thus positioned, the plunger 28 is advanced until the stop member 31 is in engagement with abutment 32 whereby the insert 21 is discharged forwardly and laterally through the opening 22. Lateral discharge is aided by the deflector cam surface 27 which urges the insert in a lateral or radial direction as the insert is forced forward to the position shown in FIG. 4B. The lateral movement is augmented by the expansion of the lead flange 24 which shifts from the flattened position shown in FIG. 4A to the expanded position shown in FIG. 4B as a result of its release from the constraints of the bore 26 of the cannula 17.

Figure 4D:
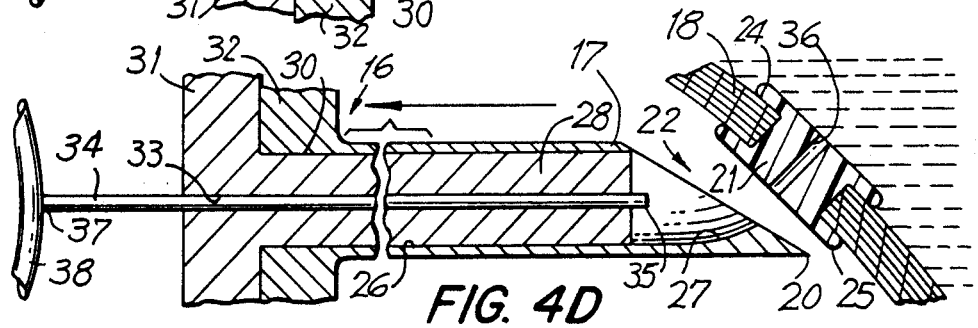

When the disposition of the components as shown in FIG. 4B is achieved it is now appropriate to withdraw the tip 35 of filament 34 from the passage 36 whereupon the parts are positioned as shown in FIG. 4C and the insert is entirely disassociated from the instrument 16. The instrument may now be withdrawn as shown in FIG. 4D leaving the implant 21 permanently positioned at the filter site in the sclera with the respective flanges 24,25 expanded at opposite sides of the sclera.

As will evident from the proceeding discussion, the passage 36 in the insert provides a permanent path for the passage of fluids from the anterior chamber through the sclera and through the bleb of the conjunctiva outwardly into the body fluids.

By way of example and without limitation, there is provided hereinbelow an indication of the desired dimensions of the various components. It should be recognized however that such dimensions shall be considered illustrative only and numerous variations and departures made therefrom to satisfy particular circumstances. The cannula 17 may have an outer diameter in the range of about 1 mm and an inner diameter of 0.65 mm. Plunger 28 which desirably is somewhat flexible may have an external diameter of 0.6 mm and incorporate an inner bore of 0.25 mm in diameter. The wire or filament 34 which preferably is readily deformable, i.e. fabricated of nylon or the like, may have an outer diameter of approximately 0.2 mm.

As respects the insert, a representative example may include an overall length of approximately 1.5 mm the length of the central or neck portion between the flanges 24,25 being approximately 1 mm. The flanges may have an overall maximum expanded diameter of approximately 1.25 mm the overall diameter being approximately 0.75 mm in the compressed (cannula encompassed) condition. A through going aperture 36 of approximately 0.25 mm will provide sufficient drainage in most cases to insure an adequately low intraocular pressure.

While the insert member 21 may be circular in transverse section, there may be instances in which an oval transverse configuration would be preferably. Specifically, there may be instances in which an oval configuration would enable the insert to be so oriented within the sclera as to minimize intrusion into the peripheral vision area while still assuring sufficient flange overlap of the respective sclera surfaces as to ensure against dislodgement of the implant.

As will be apparent to skilled workers in the art familiarized with the instant disclosure numerous variations in details such as the dimensions, materials, and structural specifics will readily occur. Accordingly, the invention is to be broadly construed within the scope of the appended claims.

We claim:

1. Apparatus for effecting a trans-scleral drain implant for the permanent treatment of glaucoma comprising a cannula having an elongate bore leading to a discharge tip, an opening formed at said tip said opening being angularly oriented relative to said bore, a resilient polymeric drain implant disposed within said cannula adjacent said tip, said implant including a drain passage extending between the ends thereof, said implant including a central neck portion and flanges adjacent said ends, said flanges projecting radially outwardly beyond said neck portion in an unstressed condition of said implant, said flanges being maintained in a radially inwardly deflected position within said bore, and discharge means for shifting said implant outwardly through said opening of said tip in a direction angularly offset from said longitudinal axis of said cannula.

2. Apparatus in accordance with claim 1 wherein said discharge means includes a deflector cam adjacent said tip having a cam surface directed toward said opening.

3. Apparatus in accordance with claim 2 wherein said discharge means includes plunger means slidably mounted in said bore for shifting said implant through said opening of said tip.

4. Apparatus in accordance with claim 3 and including resilient filament means extending through said plunger and said drain passage of said implant, said implant being frictionally supported on said filament.

5. Apparatus in accordance with claim 1 wherein said discharge means includes plunger means slidably mounted in said bore for shifting said implant through said opening of said tip.

6. Apparatus in accordance with claim 5 and including resilient filament means extending through said plunger and said drain passage of said implant, said implant being frictionally supported on said filament.

7. Apparatus in accordance with claim 1 wherein said discharge tip includes a sharpened lead cutting edge.

8. Apparatus for effecting a trans-scleral drain implant for the permanent treatment of glaucoma comprising a cannula having an elongate bore leading to a discharge tip, an opening formed at said tip, a resilient polymeric drain implant disposed within said cannula adjacent said tip said implant including a drain passage extending between the ends thereof, said implant including a narrow neck portion and flanges projecting radially outwardly beyond said neck portion in the unstressed condition of said implant, said flanges being maintained in a radially inwardly deflected position within said bore, and plunger means axially movably mounted within said bore for shifting said implant outwardly through said opening.

9. Apparatus in accordance with claim 8 and including resilient filament means extending through said plunger and said drain passage of said implant, said implant being frictionally supported on said filament.

10. Apparatus in accordance with claim 9 wherein said opening of said discharge tip is angularly oriented relative to the axis of said bore, the combination including deflector cam means adjacent said tip having a cam surface directed toward said opening.

* * * * *